United States Patent
Beattie et al.

(10) Patent No.: US 8,404,711 B2
(45) Date of Patent: Mar. 26, 2013

(54) 5-HT₄ RECEPTOR AGONIST COMPOUNDS FOR TREATMENT OF COGNITIVE DISORDERS

(75) Inventors: David Beattie, Belmont, CA (US); Fei Shen, South San Francisco, CA (US); Jacqueline A. M. Smith, Redwood City, CA (US)

(73) Assignee: Theravance, Inc., South San Francisco, CA (US)

( * ) Notice: Subject to any disclaimer, the term of this patent is extended or adjusted under 35 U.S.C. 154(b) by 379 days.

(21) Appl. No.: 12/758,631

(22) Filed: Apr. 12, 2010

(65) Prior Publication Data
US 2010/0261752 A1 Oct. 14, 2010

Related U.S. Application Data

(60) Provisional application No. 61/292,559, filed on Jan. 6, 2010, provisional application No. 61/168,741, filed on Apr. 13, 2009.

(51) Int. Cl.
*A61K 31/439* (2006.01)
*A61K 31/4545* (2006.01)
(52) U.S. Cl. .................. 514/304; 514/316
(58) Field of Classification Search .............. 514/304, 514/316
See application file for complete search history.

(56) References Cited

U.S. PATENT DOCUMENTS 7,375,114 B2   5/2008  Marquess et al.
7,598,265 B2   10/2009 Dhanoa et al.
7,759,363 B2   7/2010  McKinnell et al.

FOREIGN PATENT DOCUMENTS
WO        2006108127 A2    10/2006

OTHER PUBLICATIONS

Ansanay H. et al., "cAMP-dependent, long-lasting inhibition of a K+ current in mammalian neurons", Proc Natl Acad Sci U S A 92:6635-6639 (1995).
Beattie DT et al., "TD-8954 is a highly potent and selective 5-HT4 receptor agonist with potential utility in disorders of reduced gastrointestinal motility", Digestive Disease Week abstract #436783 (2008).
Consolo S et al., "5-HT4 receptor stimulation facilitates acetylcholine release in rat frontal cortex", Neuroreport 5:1230-1232 (1994).
Kasa P et al., "The cholinergic system in Alzheimer's disease", Prog Neurobiol 52:511-535 (1997).
Lamirault L et al., "Enhancement of place and object recognition memory in young adult and old rats by RS 67333, a partial agonist of 5-HT4 receptors", Neuropharmacology 41:844-853 (2001).
Lezoualc'h F et al., "The serotonin 5-HT4 receptor and the amyloid precursor protein processing", Exp Gerontol 38:159-166 (2003).
Robert SJ et al., "The human serotonin 5-HT4 receptor regulates secretion of non-amyloidogenic precursor protein", J Biol Chem 276:44881-44888 (2001).
Smith JA et al., "The in vitro pharmacological profile of TD-5108, a selective 5-HT(4) receptor agonist with high intrinsic activity", Naunyn Schmiedebergs Arch Pharmacol 378:125-137 (2008).
Torres GE et al., "Cyclic AMP and protein kinase A mediate 5-hydroxytryptamine type 4 receptor regulation of calcium-activated potassium current in adult hippocampal neurons", Mol Pharmacol 47:191-197 (1995).
Turner PR et al., "Roles of amyloid precursor protein and its fragments in regulating neural activity, plasticity and memory", Prog Neurobiol 70:1-32 (2003).
Yamaguchi T et al., "Evidence for 5-HT4 receptor involvement in the enhancement of acetylcholine release by p-chloroamphetamine in rat frontal cortex", Brain Res 772:95-101 (1997).
Yamaguchi T et al., "Facilitation of acetylcholine release in rat frontal cortex by indeloxazine hydrochloride: involvement of endogenous serotonin and 5-HT4 receptors", Naunyn Schmiedebergs Arch Pharmacol 356:712-720 (1997).
Al-Shamani Asma et al., "Society for Neuroscience—39th Annual Meeting. Part 2—Novel Therapies for Neurodegenerative Disorders and other CNS Diseases", IDrugs: The Investigational Drugs Journal, Dec. 2009, vol. 12 No. 12, pp. 734-737.
Ferrer et al., "Towards Early Detection and Treatment of Alzheimer's Disease: Highlights from the 11th Internationla Conference on Alzheimer's Disease and Related Disorders (ICAD)", Drugs of the Future, vol. 33, No. 9, pp. 811-822, Sep. 1, 2008.
Lamirault L et al., "Combined Treatment with Galanthaminium Bromide, A New Cholinesterase Inhibitor, and RS 67333, A Partial Agonist of 5-HT4 Receptors, Enhances Place and Object Recognition in Young Adult and Old Rats", Progress in Neuro-Psychopharmacology & Biological Phychiatry, vol. 27, No. 1, pp. 185-195, Feb. 1, 2003.
Micale V et al., "Cognitive Effects of SL65.0155, A Serotonin 5-HT4 Receptor Partial Agonist, in Animal Models of Amnesia", Brain Research, vol. 1121, No. 1, pp. 207-215, Nov. 25, 2006.
Smith C P et al., "Pharmacological Activity and Safety Profile of P10358, A Novel, Orally Active Acetylcholinesterase Inhibitor for Alzheimer's Disease", Journal of Pharmacology and Experimental Therapeutics, American Society for Pharmacology and Experimental Therapeutics, vol. 280, No. 2, pp. 710-720, Feb. 1, 1997.
Spencer J P et al., "Modulation of Hippocampal Excitability by 5-HT4 Receptor Agonists Persists in a Transgenic Model of Alzheimer's Disease", Neuroscience, vol. 129, No. 1, pp. 49-54, Jan. 1, 2004.
International Search Report for PCT/US2010/030760.
Alt et al., "PRX-03140, a partial 5-HT4 agonist, potentiates the memory enhancing effect of an efficacious dose of donepezil on delayed spontaneous alternation", 37th Annual Meeting of Society for Neuroscience, Abstract 745.10, Nov. 3-7, San Diego (2007).
Magerian, "Results of a phase 2A study of a novel 5HT4 agonist for the treatment of Alzheimer's Disease", Mar. 28, 2008.

(Continued)

*Primary Examiner* — Jennifer M Kim
(74) *Attorney, Agent, or Firm* — Jeffrey A. Hagenah; Roberta P. Saxon

(57) ABSTRACT

The invention provides methods for the treatment of cognitive disorders utilizing specific 5-HT₄ receptor agonist compounds, in particular, methods utilizing these compounds in combination with other agents, specifically acetylcholinesterase inhibitors, for the treatment of Alzheimer's disease and other cognitive disorders.

4 Claims, 3 Drawing Sheets

OTHER PUBLICATIONS

Magerian, "Results of a phase 2A study of a novel 5HT4 agonist for the treatment of Alzheimer's Disease", Jul. 30, 2008.

Shacham, "Stimulation of serotonin type 4 receptors leads to increases in alpha-secreatase activity and sAPPalpha: potential for disease modification in Alzheimer's Disease", ICAD, Jul. 29, 2008.

Chang et al., "The 5-HT4 receptor agonists, TD-5108 and TD-8954, stimulate secretion of sAPPalpha from recombinant cells expressing the human 5-HT4(d) splice variant and human APP695", Keystone Symposia Alzheimer's Disease, Copper Mountain, CO, Jan. 10-15, 2010.

Cachard-Chastel et al., "Prucalopride and donepezil act synergistically to reverse scopolamine-induced memory deficit in C57Bl/6j mice", Behavioural Brain Research 187, pp. 455-461 (2008).

Cachard-Chastel et al., "5-HT4 receptor agonists increase sAPPalpha levels in the cortex and hippocampus of male C57BL/6j mice", British Journal of Pharmacology 150, pp. 883-892 (2007).

Fontana et al., "The effects of novel, selective 5-hydroxytryptamine (5-HT)4 receptor ligands in rat spatial navigation", Neuropharmacology 36(4/5), pp. 689-696 (1997).

Langlois et al., "5-HT4 receptor ligands: applications and new prospects", Journal of Medicinal Chemistry 46(3), pp. 334-344 (2003).

Lezoualc'h, "5-HT4 receptor and Alzheimer's disease: the amyloid connection", Experimental Neurology 205, pp. 325-329 (2007).

Maillet et al., "New insights into serotonin 5-HT4 receptors: a novel therapeutic target for Alzheimer's disease?", Current Alzheimer Research 1, pp. 79-85 (2004).

Mohler et al., "VRX-03011, a novel 5-HT4 agonist, enhances memory and hippocampal acetylcholine efflux", Neuropharmacology 53, pp. 563-573 (2007).

Morris, "Developments of a water-maze procedure for studying spatial learning in the rat", Journal of Neuroscience Methods 11, pp. 47-60 (1984).

Moser et al., "SL65.0155, a novel 5-hydroxytryptamine4 receptor partial agonist with potent cognition-enhancing properties", The Journal of Pharmacology and Experimental Therapeutics 302(2), pp. 731-741 (2002).

Russo et al., "Design, synthesis, and biological evaluation of new 5-HT4 receptor agonists: application as amyloid cascade modulators and potential therapeutic utility in Alzheimer's disease", Journal of Medicinal Chemistry 52, pp. 2214-2225 (2009).

5-HT$_4$ RECEPTOR AGONIST COMPOUNDS FOR TREATMENT OF COGNITIVE DISORDERS

CROSS-REFERENCE TO RELATED APPLICATIONS

This application claims the benefit of U.S. Provisional Application Nos. 61/168,741, filed on Apr. 13, 2009, and 61/292,559, filed on Jan. 6, 2010, the disclosures of which are incorporated herein by reference in their entirety.

BACKGROUND OF THE INVENTION

1. Field of the Invention

The invention is directed to the use of specific 5-HT$_4$ receptor agonist compounds for the treatment of cognitive disorders, in particular to the use of these compounds in combination with other agents, specifically acetylcholinesterase inhibitors for the treatment of Alzheimer's disease and other cognitive disorders.

2. State of the Art

The number of elderly people at risk of developing dementia is growing rapidly as life expectancy increases around the world. Alzheimer's disease is the most common cause of dementia in the elderly, accounting for 50-60% of all cases, according to some experts. In 2008, an estimated 5.2 million people were living with Alzheimer's disease in the United States alone, accounting for 13% of the US population aged 65 and over.

Alzheimer's disease is defined as progressive cognitive decline and impaired functional status inconsistent with normal aging. It is believed that deficits in the cholinergic system are a major contributor to the cognitive symptoms associated with Alzheimer's disease. Accordingly, the dominant pharmaceutical treatment for Alzheimer's disease provides modest symptomatic relief through the use of acetylcholinesterase inhibitors. These agents are believed to act by reducing the rate of acetylcholine degradation thus leading to increases in acetylcholine concentrations in the brain.

Serotonin (5-hydroxytryptamine, 5-HT) is a neurotransmitter that is widely distributed throughout the body, both in the central nervous system and in peripheral systems. At least seven subtypes of serotonin receptors have been identified and the interaction of serotonin with these different receptors is linked to a wide variety of physiological functions. The serotonergic system in the brain has been shown to be involved in cognitive processes. In particular, 5-HT$_4$ receptors have been demonstrated to play a role in the neuronal mechanism of memory enhancement and cognitive processes in animal models. Activation of the 5-HT$_4$ receptor enhances release of acetylcholine from cholinergic neurons, thus providing another potential approach to a pharmacological intervention that beneficially increases acetylcholine concentrations at synapses within the brain (Maillet et al. (2004) *Current Alzheimer Research* 1:79-85). Furthermore, it has been suggested that some 5-HT$_4$ receptor agonist compounds may be used in the treatment of central nervous system disorders including cognitive disorders, behavioral disorders, mood disorders, such as depression and anxiety, and disorders of control of autonomic function.

Activation of the 5-HT$_4$ receptor also stimulates α-secretase activity resulting in increased levels of soluble amyloid precursor protein alpha (sAPPα) which has neurotrophic and neuroprotective properties, and is also associated with cognitive enhancement preclinically. Beta amyloid (Aβ) is a peptide of 39-43 amino acids that appears to be the main constituent of amyloid plaques in the brains of Alzheimer's disease patients. Aβ is formed after cleavage of amyloid precursor protein by β- and γ-secretases. In preclinical studies, 5-HT$_4$ receptor agonist-induced activation of α-secretase, and generation of sAPPα, reduces the level of Aβ. Such a reduction in Aβ levels is expected to be beneficial. Therefore, 5-HT$_4$ receptor agonists offer the potential to provide both symptomatic and disease-modifying benefits (Lezoualc'h (2007) *Experimental Neurology* 205:325-329).

To date, no treatment that exploits the potential utility of the 5-HT$_4$ mechanism for the treatment of cognitive disorders has been approved. Accordingly there remains a need for a treatment of memory dysfunction in people suffering from Alzheimer's disease that takes advantage of increases in acetylcholine concentrations and other potential benefits expected from use of a 5-HT$_4$ receptor agonist agent.

SUMMARY OF THE INVENTION

The invention relates to the use of specific 5-HT$_4$ receptor agonist compounds and to the use of specific 5-HT$_4$ receptor agonist compounds in combination with an acetylcholinesterase inhibitor for the treatment of Alzheimer's disease or a cognitive disorder. In particular, the invention relates to the use of the 5-HT$_4$ receptor agonist compounds and an acetylcholinesterase inhibitor, where each agent is used at a concentration below the concentration at which a significant effect can be observed when used alone.

The 5-HT$_4$ receptor agonist, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide (1) and pharmaceutically-acceptable salts thereof

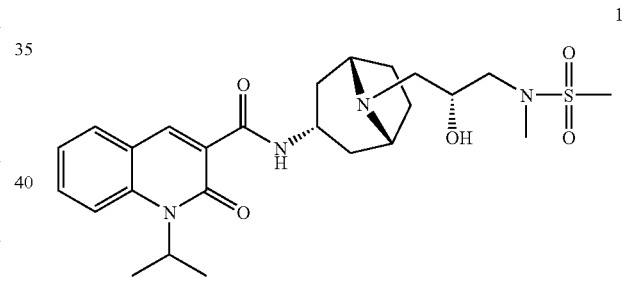

are disclosed in U.S. Pat. No. 7,375,114 B2. Compound 1 is alternatively denoted as 1,2-dihydro-N-[(3-endo)-8-[(2R)-2-hydroxy-3-[methyl(methylsulfonyl)amino]propyl]-8-azabicyclo[3.2.1]oct-3-yl]-1-(1-methylethyl)-2-oxo-3-quinolinecarboxamide.

The 5-HT$_4$ receptor agonist, 4-(4-{[(2-isopropyl-1H-benzoimidazole-4-carbonyl)amino]methyl}-piperidin-1-ylmethyl)piperidine-1-carboxylic acid methyl ester (2) and pharmaceutically-acceptable salts thereof

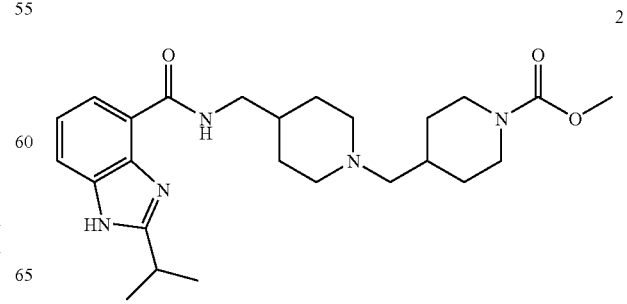

are disclosed in U.S. Pat. No. 7,256,294 B2 and US2006/0270652 A1. Compound 2 is alternatively denoted as 4-[[4-[[[[2-(1-methylethyl)-1H-benzimidazol-7-yl]carbonyl]amino]methyl]-1-piperidinyl]methyl]-1-piperidinecarboxylic acid methyl ester.

Compounds 1 and 2 are potent and selective 5-$HT_4$ receptor agonists that demonstrate moderate to high intrinsic activity in in vitro assays. Compounds 1 and 2 have each been demonstrated to attenuate a muscarinic antagonist-induced memory deficit in the rat Morris water maze preclinical cognition model. Results consistent with an additive or synergistic effect were observed between compound 1 and the acetylcholinesterase inhibitor donepezil and between compound 2 and donepezil at doses that on their own had little or no effect. Compounds 1 and 2 have also been shown to evoke a concentration-dependent increase in sAPPα in in vitro assays. Compounds 1 and 2 are therefore expected to be beneficial in the treatment of memory dysfunction.

In one aspect, the invention provides a method of treating Alzheimer's disease or a cognitive disorder in a patient, the method comprising administering to the patient a 5-$HT_4$ receptor agonist compound wherein the compound is selected from 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide and 4-(4-{[(2-isopropyl-1H-benzoimidazole-4-carbonyl)amino]methyl}-piperidin-1-ylmethyl)piperidine-1-carboxylic acid methyl ester, and pharmaceutically acceptable salts thereof.

The present 5-$HT_4$ agonist compounds are beneficially used in combination with an agent that acts to inhibit the action of acetylcholinesterase in the body. Useful inhibitors include, but are not limited to, donepezil hydrochloride (available commercially as Aricept®), galantamine hydrobromide, alternatively written galanthamine hydrobromide (Razadyne®, Reminyl®), rivastigmine tartrate (Exelon®), and tacrine hydrochloride (Cognex®).

In another aspect, the invention provides a method of treating Alzheimer's disease or a cognitive disorder in a patient, the method comprising administering to the patient a 5-$HT_4$ receptor agonist compound wherein the compound is selected from 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide and 4-(4-{[(2-isopropyl-1H-benzoimidazole-4-carbonyl)amino]methyl}-piperidin-1-ylmethyl)piperidine-1-carboxylic acid methyl ester, and pharmaceutically acceptable salts thereof and an acetylcholinesterase inhibitor.

In one aspect of the invention, in the above method, the 5-$HT_4$ agonist compound and the acetylcholinesterase inhibitor are each administered at a dose that is subefficacious for treating Alzheimer's disease or a cognitive disorder when administered alone.

In a specific aspect, the 5-$HT_4$ receptor agonist compound is 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide hydrochloride and the acetylcholinesterase inhibitor is donepezil.

In another specific aspect, the 5-$HT_4$ receptor agonist compound is 4-(4-{[(2-isopropyl-1H-benzoimidazole-4-carbonyl)amino]methyl}-piperidin-1-ylmethyl)piperidine-1-carboxylic acid methyl ester and the acetylcholinesterase inhibitor is donepezil.

In yet another aspect, the invention provides a method of enhancing memory in a patient experiencing a memory deficit, the method comprising administering to the patient a 5-$HT_4$ receptor agonist compound wherein the compound is selected from 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide and 4-(4-{[(2-isopropyl-1H-benzoimidazole-4-carbonyl)amino]methyl}-piperidin-1-ylmethyl)piperidine-1-carboxylic acid methyl ester, and pharmaceutically acceptable salts thereof and an acetylcholinesterase inhibitor.

In one aspect, the 5-$HT_4$ agonist compound and the acetylcholinesterase inhibitor are each administered at a dose that is subefficacious for enhancing memory in a patient experiencing a memory deficit when administered alone.

As increase of sAPPα levels has been associated with cognitive enhancement, in yet another aspect, the invention provides a method of increasing the levels of sAPPα in a patient, the method comprising (a) identifying a patient in need of increased production of sAPPα, i.e. a patient suffering from cognitive impairment, and (b) administering to the patient a therapeutically-effective amount of a 5-$HT_4$ receptor agonist compound wherein the compound is selected from 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide and 4-(4-{[(2-isopropyl-1H-benzoimidazole-4-carbonyl)amino]methyl}-piperidin-1-ylmethyl)piperidine-1-carboxylic acid methyl ester, and pharmaceutically acceptable salts thereof.

The invention further provides a pharmaceutical composition comprising a pharmaceutically-acceptable carrier, a 5-$HT_4$ receptor agonist compound, wherein the compound is selected from 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide and 4-(4-{[(2-isopropyl-1H-benzoimidazole-4-carbonyl)amino]methyl}-piperidin-1-ylmethyl)piperidine-1-carboxylic acid methyl ester, and pharmaceutically acceptable salts thereof, and an acetylcholinesterase inhibitor.

BRIEF DESCRIPTION OF THE DRAWINGS

Various aspects of the present invention are illustrated by reference to the accompanying drawings.

FIG. 1 shows results for administration of vehicle, scopolamine (Scop) (0.5 mg/kg), donepezil (0.3 mg/kg) plus scopolamine (0.5 mg/kg), donepezil (1 mg/kg) plus scopolamine (0.5 mg/kg), and donepezil (3 mg/kg) plus scopolamine (0.5 mg/kg). * statistically significant with respect to vehicle (student t-test with Bonferroni adjustment $p<0.025$) # statistically significant with respect to scopolamine (0.5 mg/kg) (one-way ANOVA for scopolamine (0.5 mg/kg) and all doses of donepezil plus scopolamine (0.5 mg/kg), post-hoc Dunnett's test $p<0.05$).

FIG. 2 shows results for administration of vehicle, scopolamine (Scop) (0.5 mg/kg), donepezil (3 mg/kg) plus scopolamine (0.5 mg/kg), compound 1 (0.01 mg/kg) plus scopolamine (0.5 mg/kg), compound 1 (0.03 mg/kg) plus scopolamine (0.5 mg/kg), compound 1 (0.1 mg/kg) plus scopolamine (0.5 mg/kg) and compound 1 (0.1 mg/kg) plus scopolamine (0.5 mg/kg). *** statistically significant with respect to vehicle (student t-test with Bonferroni adjustment $p<0.0005$) # statistically significant with respect to scopolamine (0.5 mg/kg) (one-way ANOVA for scopolamine (0.5 mg/kg) and all doses of compound 1 plus scopolamine (0.5 mg/kg), post-hoc Dunnett's test $p<0.05$).

FIG. 3 shows results for administration of vehicle, scopolamine (Scop) (0.5 mg/kg), GR125487 (1 mg/kg), compound 1 (0.1 mg/kg) plus GR125487 (1 mg/kg) and scopolamine (0.5 mg/kg), and compound 1 (0.1 mg/kg) plus scopolamine (0.5 mg/kg). * statistically significant with respect to vehicle (student t-test with Bonferroni adjustment p<0.025) †† statistically significant with respect to compound 1 (0.1 mg/kg) plus GR125487 (1 mg/kg) and scopolamine (0.5 mg/kg) (student t-test with Bonferroni adjustment p<0.005) # statistically significant with respect to scopolamine (0.5 mg/kg) (student t-test with Bonferroni adjustment p<0.025).

FIG. 4 shows results for administration of vehicle, scopolamine (Scop) (0.5 mg/kg), donepezil (0.1 mg/kg) plus scopolamine (0.5 mg/kg), compound 1 (0.01 mg/kg) plus scopolamine (0.5 mg/kg), and compound 1 (0.01 mg/kg) plus donepezil (0.1 mg/kg) and scopolamine (0.5 mg/kg) * statistically significant with respect to vehicle (student t-test p<0.05)

FIG. 5 shows results for administration of vehicle, scopolamine (Scop) (0.5 mg/kg), donepezil (3 mg/kg) plus scopolamine (0.5 mg/kg), compound 2 (0.01 mg/kg) plus scopolamine (0.5 mg/kg), compound 2 (0.03 mg/kg) plus scopolamine (0.5 mg/kg), compound 2 (0.1 mg/kg) plus scopolamine (0.5 mg/kg) and compound 2 (1 mg/kg) plus scopolamine (0.5 mg/kg). *** statistically significant with respect to vehicle (student t-test with Bonferroni adjustment p<0.0005) # statistically significant with respect to scopolamine (0.5 mg/kg) (one-way ANOVA for scopolamine (0.5 mg/kg) and all doses of compound 2 plus scopolamine (0.5 mg/kg), p=0.0096 post-hoc Dunnett's test p<0.05).

FIG. 6 shows results for administration of vehicle, scopolamine (Scop) (0.5 mg/kg), donepezil (0.1 mg/kg) plus scopolamine (0.5 mg/kg), compound 2 (0.01 mg/kg) plus scopolamine (0.5 mg/kg), and compound 2 (0.01 mg/kg) plus donepezil (0.1 mg/kg) and scopolamine (0.5 mg/kg)** statistically significant with respect to vehicle (student t-test with Bonferroni adjustment p<0.005) # statistically significant with respect to scopolamine (0.5 mg/kg) (student t-test with Bonferroni adjustment p<0.025).

DETAILED DESCRIPTION OF THE INVENTION

Definitions

Figure 1:
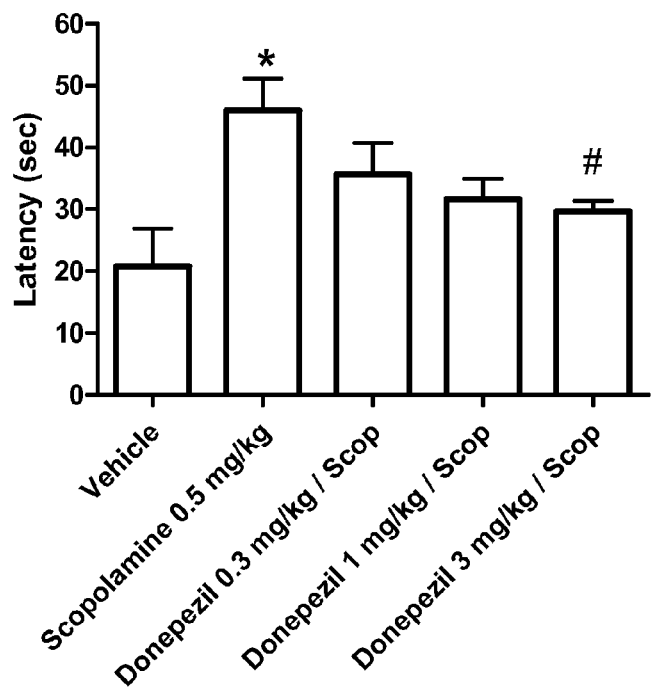
FIGS. 1 through 6 display the mean escape latency in seconds on the third test day of animals tested in the rat Morris water maze model of cognitive function.

When describing the compositions and methods of the invention, the following terms have the following meanings, unless otherwise indicated.

The term "therapeutically effective amount" means an amount sufficient to effect treatment when administered to a patient in need of treatment.

The term "subefficacious amount" or, equivalently, "subefficacious dose" means an amount or dose lower than a therapeutically effective amount or dose.

The term "treatment" as used herein means the treatment of a disease, disorder, or medical condition in a patient, such as a mammal (particularly a human) which includes, one or more of the following:

(a) preventing the disease, disorder, or medical condition from occurring, i.e., prophylactic treatment of a patient;
(b) ameliorating the disease, disorder, or medical condition, i.e., eliminating or causing regression of the disease, disorder, or medical condition in a patient, including counteracting the effects of other therapeutic agents;
(c) suppressing the disease, disorder, or medical condition, i.e., slowing or arresting the development of the disease, disorder, or medical condition in a patient; or
(d) alleviating the symptoms of the disease, disorder, or medical condition in a patient.

The term "combination therapy" as used herein means the administration of two or more therapeutic agents as part of a treatment protocol intended to provide beneficial effects from the combined action of the therapeutic agents.

The term "acetylcholinesterase inhibitor" as used herein means any agent that has the effect of inhibiting the action of acetylcholinesterase. The term includes agents termed cholinesterase inhibitors, which may have other activity in addition, for example as butyrylcholinesterase inhibitors.

The term "donepezil" is used herein as an equivalent to donepezil hydrochloride.

Demonstration of Cognitive Enhancement In Vivo

As further described in the following examples, the efficacy of the 5-HT$_4$ agonists, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide (1) and 4-(4-{[(2-isopropyl-1H-benzoimidazole-4-carbonyl)amino]methyl}-piperidin-1-ylmethyl)piperidine-1-carboxylic acid methyl ester (2) in reversing muscarinic antagonist-induced memory impairment in rats was evaluated in the Morris water maze model.

Compound 1 at doses of 0.03, 0.1, and 1 mg/kg and compound 2 at doses of 0.03 and 0.1 mg/kg attenuated the memory impairment induced in rats by injection of scopolamine. For both compounds, a statistically significant response was observed at 0.1 mg/kg. The potency and/or efficacy of both 5-HT$_4$ agonist compounds appeared to be similar to that of donepezil, an acetylcholinesterase inhibitor marketed for the symptomatic treatment of Alzheimer's disease. The cognitive enhancing effects of compound 1 and of compound 2 were prevented by coadministration of each compound with a selective 5-HT$_4$ antagonist, confirming involvement of 5-HT$_4$ receptors in the observed response.

Significantly, an additive or synergistic effect was noted between compound 1 and donepezil at doses of 0.01 mg/kg and 0.1 mg/kg, respectively, and between compound 2 and donepezil at doses of 0.01 mg/kg and 0.1 mg/kg, respectively, doses that were not effective at reversing scopolamine-induced cognitive decline when administered alone.

Demonstration of sAPPα Release In Vitro

The effects of compounds 1 and 2 on extracellular release of sAPPα was studied in HEK293 cells stably-transfected with human 5-HT$_{4(d)}$ receptors and human APP$_{695}$ (amyloid precursor protein). Both compounds evoked a concentration-dependent increase in sAPPα release. The release was blocked by the 5-HT$_4$ receptor-selective antagonist GR113808, indicating that the observed effect is related to agonism of the 5-HT$_4$ receptor.

Methods of Treatment

The present 5-HT$_4$ agonists, compounds 1 and 2, are expected to be useful for the treatment of Alzheimer's disease or a cognitive disorder, including treatment of mild cognitive impairment, and treatment of memory dysfunction associated with Alzheimer's disease and of dementia of the Alzheimer's type. The compounds may further find utility in the treatment of additional central nervous system disorders including behavioral disorders, mood disorders, such as depression and anxiety, and disorders of control of autonomic function. In addition, it has been suggested that compounds that enhance acetylcholine concentrations may also be useful for the treatment of other forms of dementia, such as dementia associated with Parkinson's disease, dementia due to vascular mechanisms, and Lewy body dementia.

An additive or synergistic effect was noted in the rat water maze experiments when the present 5-HT$_4$ compounds were coadministered with an acetylcholinesterase inhibitor at doses where each compound was ineffective when administered alone. Accordingly, the present compounds are expected to be useful for the treatment of Alzheimer's disease or a cognitive disorder, when administered in combination with an acetylcholinesterase inhibitor such as donepezil hydrochloride (Aricept®), galantamine hydrobromide, (Razadyne®, Reminyl®), rivastigmine tartrate (Exelon®), or tacrine hydrochloride (Cognex®). In addition to providing the benefit of agents acting by different, complementary mechanisms of action, combination therapy offers the additional potential benefit of allowing lower dosages of each agent to be used, thus limiting exposure to any adverse side effects.

Further, compounds 1 and 2 may be useful when coadministered with agents designed to provide symptomatic therapy to Alzheimer's patients by yet other mechanisms of action. For example the present compounds may be useful in combination with memantine (Namenda®), an NMDA receptor antagonist. Additional agents that may be used in combination for the treatment of Alzheimer's disease include $5-HT_6$ antagonists such as DMXB-anabaseine, GSK-742457, SUVN-502, PRX-07034, and SAM-531 (WAY-262531); nicotinic receptor agonists, such as ABT-089, SSR-180711, AZD-0328, and EVP-6124; muscarinic $M_1$ agonists, such as NGX-267, AF-102B (Cevimeline), and WAL 2014 FU (talsaclidine); histamine $H_3$ antagonists such as GSK-189254 and PF-365474; and dimebon. Also, $5-HT_4$ agonists may be beneficial in combination with other proposed disease modifying therapies such as amyloid-beta and tau aggregation inhibitors, and beta secretase inhibitors or gamma secretase inhibitors, such as BMS-708163.

When used in combination therapy, the present $5-HT_4$ compounds are either physically mixed with the other therapeutic agent to form a composition containing both agents; or each agent is present in separate and distinct compositions which are administered to the patient simultaneously or sequentially in any order. Combination therapy includes administration of the two agents, when formulated separately, substantially at the same time, as well as administration of each agent at a different time.

For example, the present $5-HT_4$ compounds can be combined with a second therapeutic agent using conventional procedures and equipment to form a composition comprising compound 1 or compound 2 and a second therapeutic agent. Additionally, the therapeutic agents may be combined with a pharmaceutically acceptable carrier to form a pharmaceutical composition comprising compound 1 or compound 2, a second therapeutic agent, and a pharmaceutically acceptable carrier. In this embodiment, the components of the composition are typically mixed or blended to create a physical mixture. The physical mixture is then administered in a therapeutically effective amount using any of the routes described below.

Alternatively, the therapeutic agents may remain separate and distinct before administration to the patient. In this embodiment, the agents are not physically mixed together before administration but are administered simultaneously or at separate times as separate compositions. Such compositions can be packaged separately or may be packaged together as a kit. The two therapeutic agents in the kit may be administered by the same route of administration or by different routes of administration.

When used to treat Alzheimer's disease or cognitive disorders, compound 1 or compound 2 will typically be administered orally in a single daily dose or in multiple doses per day, although other forms of administration may be used. In certain circumstances, it may be beneficial to administer the present $5-HT_4$ compounds transdermally or parenterally. The amount of active agent administered per dose or the total amount administered per day will typically be determined by a physician, in the light of the relevant circumstances, including the severity of the condition to be treated, the chosen route of administration, the specific compound administered and its relative activity, the age, weight, and response of the individual patient, and the like.

Suitable doses for treating Alzheimer's disease or cognitive disorders will range from about 0.1 to about 90 mg per day of $5-HT_4$ agonist agent for an average 70 kg human, including, for example, from about 1 to about 50 mg per day of compound 1, and from about 0.5 to about 20 mg per day of compound 2.

When the present $5-HT_4$ compounds are used in combination therapy with an acetylcholinesterase inhibitor, the acetylcholinesterase inhibitor is administered in a therapeutically effective amount, i.e. in any amount that produces a therapeutically beneficial effect when co-administered with compound 1 or compound 2. Suitable doses for the acetylcholinesterase inhibitor administered in combination with the present compounds are typically in the range of about 1 mg/day to about 30 mg/day. As described previously, when used as part of combination therapy, an effective dose of each individual agent may be lower than the effective dose when the agents are used independently.

Pharmaceutical Compositions

The present $5-HT_4$ agonists and the other therapeutic agents, such as acetylcholinesterase inhibitors, are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration.

The pharmaceutical compositions typically contain a therapeutically effective amount of the active agents. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; preferably, from about 5 to about 70% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a therapeutic compound as an active ingredient.

When intended for oral administration in a solid dosage form (i.e., as capsules, tablets, pills and the like), the pharmaceutical compositions will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Coating agents also include talc, polyethylene glycol, hypomellose and titanium dioxide.

Pharmaceutical compositions may also be formulated to provide slow or controlled release of the active agent using, by way of example, hydroxypropyl methyl cellulose in varying proportions; or other polymer matrices, liposomes and/or microspheres. In addition, pharmaceutical compositions may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The present active agents can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the agents are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

Finally, active agents can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Representative pharmaceutical compositions useful for the treatment of Alzheimer's disease or a cognitive disorder, include, but are not limited to, the following examples where 'compound of the invention' represents compound 1 or compound 2. Compound 1 is typically supplied as a hydrochloride salt and compound 2 is typically supplied as a free base, but it will be understood that any form of the compounds (i.e. free base or pharmaceutical salt) that is suitable for the particular mode of administration, can be used in the following pharmaceutical compositions.

FORMULATION EXAMPLE A

Hard Gelatin Capsules for Oral Administration

A compound of the invention (20 mg), starch (89 mg), microcrystalline cellulose (89 mg), and magnesium stearate (2 mg) are thoroughly blended and then passed through a No. 45 mesh U.S. sieve. The resulting composition is loaded into a hard gelatin capsule (200 mg of composition per capsule).

FORMULATION EXAMPLE B

Gelatin Capsules for Oral Administration

A compound of the invention (10 mg), polyoxyethylene sorbitan monooleate (50 mg), and starch powder (250 mg) are thoroughly blended and then loaded into a gelatin capsule (310 mg of composition per capsule).

FORMULATION EXAMPLE C

Tablets for Oral Administration

A compound of the invention (5 mg), microcrystalline cellulose (400 mg), fumed silicon dioxide (10 mg), and stearic acid (5 mg) are thoroughly blended and then compressed to form tablets (420 mg of composition per tablet).

FORMULATION EXAMPLE D

Tablets for Oral Administration

A compound of the invention (2 mg), microcrystalline cellulose (400 mg), fumed silicon dioxide (10 mg), and stearic acid (5 mg) are thoroughly blended and then compressed to form tablets (417 mg of composition per tablet).

FORMULATION EXAMPLE E

Tablets for Oral Administration

A compound of the invention (20 mg), microcrystalline cellulose (400 mg), fumed silicon dioxide (10 mg), and stearic acid (5 mg) are thoroughly blended and then compressed to form tablets (435 mg of composition per tablet).

FORMULATION EXAMPLE F

Single-Scored Tablets for Oral Administration

A compound of the invention (15 mg), cornstarch (50 mg), croscarmellose sodium (25 mg), lactose (120 mg), and magnesium stearate (5 mg) are thoroughly blended and then compressed to form single-scored tablet (215 mg of compositions per tablet).

FORMULATION EXAMPLE G

Suspension for Oral Administration

The following ingredients are thoroughly mixed to form a suspension for oral administration containing 20 mg of active ingredient per 10 mL of suspension: compound of the invention (200 mg), sodium benzoate, sodium citrate, purified water (q.s. to 100 mL).

FORMULATION EXAMPLE H

Injectable Formulation

A compound of the invention (20 mg) is blended with 0.1 M sodium citrate buffer solution (15 mL). The pH of the resulting solution is adjusted to pH 6 using 1 N aqueous hydrochloric acid or 1 N aqueous sodium hydroxide. Sterile normal saline in citrate buffer is then added to provide a total volume of 20 mL.

FORMULATION EXAMPLE I

Single-Scored Tablets for Oral Administration

A compound of the invention (5 mg), donepezil hydrochloride (5 mg), cornstarch (50 mg), microcrystalline cellulose (15 mg), hydroxypropyl cellulose (10 mg) lactose (120 mg), and magnesium stearate (5 mg) are thoroughly blended and then compressed to form single-scored tablet (210 mg of compositions per tablet).

FORMULATION EXAMPLE J

Suspension for Oral Administration

The following ingredients are thoroughly mixed to form a suspension for oral administration containing 5 mg of each agent per 10 mL of suspension: compound of the invention (50 mg), rivastigmine tartrate (50 mg) sodium benzoate, sodium citrate, purified water (q.s. to 100 mL).

EXAMPLES

The ability of the 5-HT$_4$ agonists, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide (1) and 4-(4-{[(2-isopropyl-1H-benzoimidazole-4-carbonyl)amino]methyl}-piperidin-1-ylmethyl)piperidine-1-carboxylic acid methyl ester and (2), used alone or in combination with the acetylcholinesterase inhibitor, donepezil, to prevent spatial memory impairment induced by the muscarinic receptor antagonist, scopolamine, was evaluated in the rat Morris water maze animal model (Morris (1984) *Journal of Neuroscience Methods* 11:47-60.). The hydrochloride salt of compound 1 was used in all experiments.

Morris Water Maze Model Methodology

Adult, male Sprague-Dawley rats (body weight range 275-400 g) were handled by the investigator for approximately 5 minutes one day prior to each study. On the first study day, each rat was dosed intraperitoneally (i.p.), first with test compound or vehicle, followed immediately thereafter with the muscarinic receptor antagonist, scopolamine (0.5 mg/kg), a dose previously identified to provide a near-maximal cognitive decline in this model) or vehicle. Thirty minutes after dosing, rats were placed individually into a circular, dark blue polyethylene tank (6 feet in diameter) filled with water (maintained at 23° C.±1° C.). A clear Perspex® platform was located in a fixed position 1 cm below the surface of the water, and 34 cm from the wall of the tank. Four visual cues (A4-sized pictures of different black and white symbols) were equally spaced on the wall of the tank, just above the water surface. Black curtains were placed around the tank and white noise was generated throughout the test. Each rat was released into the water, facing the tank wall, at a designated starting point (i.e., at the north side of the tank), and allowed 60 seconds to locate the submerged platform after each placement. The escape latency (in seconds) between release of the rat into the water and its locating the platform was recorded automatically by means of a video camera (San Diego Instrument, CA) and tracking software (SMART software, San Diego Instrument, CA). When a rat failed to find the platform within 60 seconds, it was guided towards the platform and then placed on it (facing a specific visual cue). The rats were allowed to remain on the platform for 30 seconds to observe the external visual cues and pair them with the relative position of the platform. The rats were then taken off the platform and dried gently with a paper towel before repeating the test three more times (from south, then east and finally west starting positions). After the fourth test, each rat was placed under a heating lamp for 5 minutes before being returned to its home cage. The entire procedure was repeated on days 2 and 3. Over the three days of testing, rats learned to associate the location of the submerged platform (and their only means to escape the water) with the visual cues.

The ability of test agents to inhibit scopolamine-induced cognitive impairment was evaluated. On day 4, each rat was dosed as before and subjected to a 2-minute "probe trial", for which the platform had been removed from the tank. The number of crossings of the previous platform location and the time spent by the rat in each quadrant were recorded. Animals that had learned the location of the platform spent more time in the appropriate quadrant and repeatedly crossed that quadrant. By performing the probe test, false positives could be excluded from the analysis (i.e., rats that had previously located the platform via a strategy independent of the visual cues, such as swimming randomly until a leg hit the platform). No animals were excluded based on conflicting data between the three days of testing and the probe test.

Data Analysis

The average escape latency from each of the four trials on the same test day was calculated for individual rats, and then these data were combined to determine the mean escape latency for each treatment group on days 1, 2 and 3. The following statistical tests were performed on the data:

A student's t-test compared the escape latencies of the vehicle/vehicle and vehicle/scopolamine groups. The a value was Bonferroni adjusted to 0.025 as the vehicle/scopolamine group was subjected to both a Student's t-test and a one-way ANOVA test.

A one-way ANOVA, followed by a Dunnett's post-hoc test, was used to compare the escape latencies of the vehicle/scopolamine and test compound/scopolamine groups, with $p<0.05$ indicating a statistically significant difference.

A two-way repeated-measures ANOVA, followed by a Bonferroni post-hoc test, was used to compare the mean escape latency for each of the three successive test days, with $p<0.05$ indicating a statistically significant difference.

Materials

The $5-HT_4$ agonist compounds 1 and 2 were prepared according to the procedures described in U.S. Pat. No. 7,375,114 B2 and U.S. Pat. No. 7,256,294 B2, respectively, the disclosures of which are incorporated herein by reference. Donepezil hydrochloride was purchased from Changzhou Dahua Imp. and Exp. Corp. Ltd. (Changzhou, Jiangsu, China) while scopolamine hydrochloride was purchased from Sigma Aldrich (St. Louis, Mo.) or Spectrum Chemical Mfg. Corp. (Gardena, Calif.). GR125487 sulfamate was purchased from Tocris (Ellisville, Mo.). Compounds 1 and 2 and donepezil were formulated in 5% dimethyl sulfoxide and 95% sterile saline, while scopolamine and GR125487 were prepared in 100% sterile saline. Doses were expressed with respect to the free base weights of each compound.

Model Validation

In each study, dosing (i.p.) of rats with vehicle 30 min prior to the test resulted in a progressive reduction in escape latency. On day 1, vehicle-treated rats typically located the hidden platform with a mean latency from the four trials in the range of 40-50 seconds, while on day 3, this had shortened to 10-25 seconds. Scopolamine (0.5 mg/kg i.p.) produced a statistically significant attenuation of learning ($p<0.025$, Student's t-test with Bonferroni's adjustment) as compared with vehicle treated animals. The acetylcholinesterase inhibitor donepezil (3 mg/kg i.p.), and the $5-HT_4$ receptor agonists, compound 1 (1 mg/kg i.p.) and compound 2 (1 mg/kg i.p.), had no effect, either positive or negative, on the ability of rats to learn the location of the submerged platform when administered alone, i.e. when administered to animals that had not been exposed to scopolamine. Donepezil (0.3-3 mg/kg i.p.), reversed the scopolamine (0.5 mg/kg i.p.)-induced cognitive deficit in a dose-dependent manner as shown in FIG. 1 where the mean escape latency on the third test day is displayed. The donepezil dose at 3 mg/kg produced a statistically significant reversal.

Example 1

The Effect of Compound 1 on Scopolamine-Induced Cognitive Impairment

Figure 2:
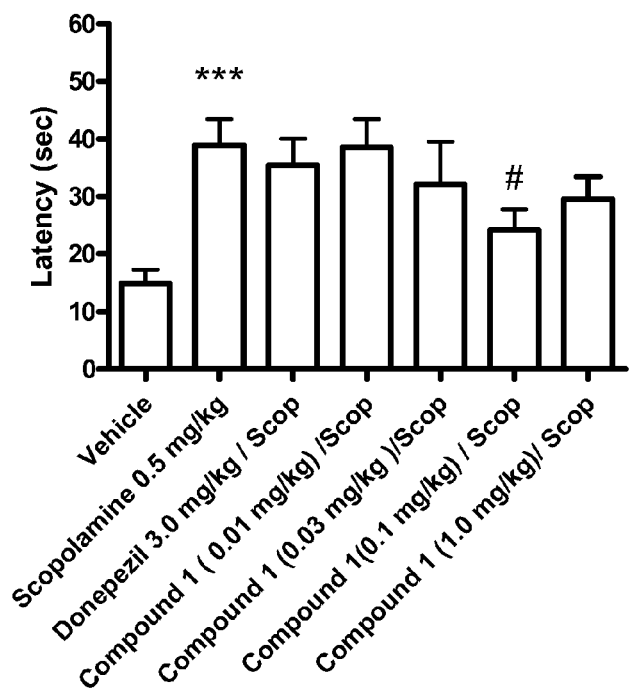

Compound 1 was tested at doses of 0.01, 0.03, 0.1, and 1 mg/kg in the rat Morris Water Maze model. As shown in FIG. 2, where the mean escape latency on the third test day is displayed, compound 1 was associated with reversal of the memory impairment produced by 0.5 mg/kg scopolamine. The effect of compound 1, at a dose of 0.1 mg/kg, achieved statistical significance with respect to scopolamine (0.5 mg/kg). A "U-shaped" dose-response curve was evident; the highest dose of compound 1, 1 mg/kg, had no effect on the scopolamine-induced response unlike the 0.1 mg/kg dose. Compound 1 (0.1 mg/kg i.p.) produced a similar reversal to that of donepezil (3 mg/kg i.p.) on day 3 (i.e., in the range of 50-60%, see FIG. 1)

Example 2

Figure 3:
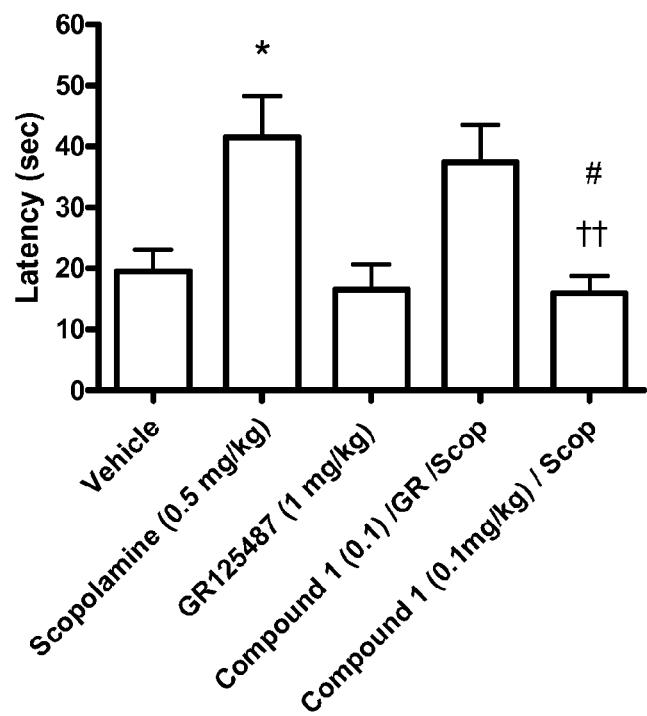

The Effect of Compound 1 Together with a 5-HT$_4$ Receptor Antagonist on Scopolamine-Induced Cognitive Impairment In order to probe whether the observed effects of compound 1 can be attributed to agonism at the 5-HT$_4$ receptor, compound 1 was tested together with GR125487, a selective 5-HT$_4$ receptor antagonist compound. As shown in FIG. 3, GR125487 (1 mg/kg i.p.) had no effect when administered alone. However, coadministration of the antagonist GR125487 (1 mg/kg i.p.) abolished the ability of compound 1 (0.1 mg/kg i.p.) to reverse scopolamine-induced cognitive impairment. Therefore, it is reasonable to conclude the observed effects of compound 1 are due to 5-HT$_4$ receptor agonism.

Example 3

Figure 4:
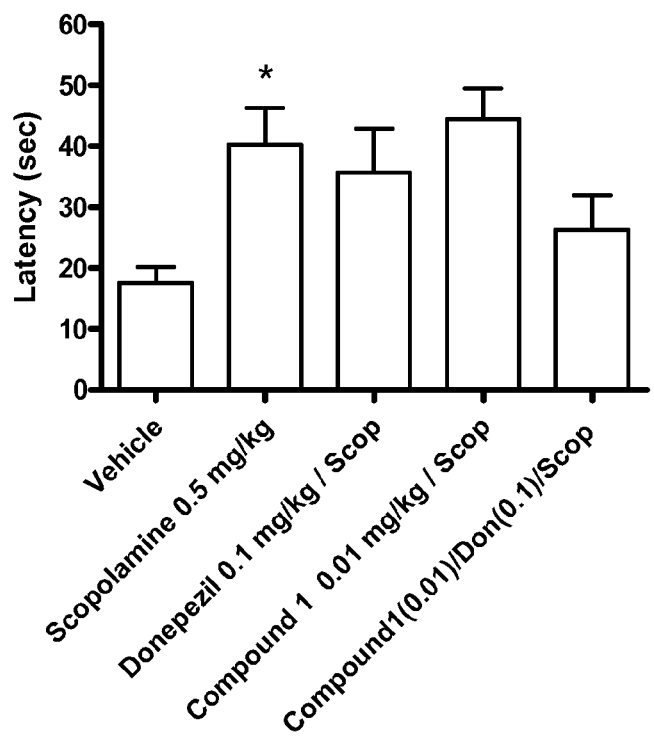

The Effect of Co-Administration of Compound 1 Together with a the Acetylcholinesterase Inhibitor Donepezil on Scopolamine-Induced Cognitive Impairment The effect of co-administration of compound 1 and donepezil is illustrated in FIG. 4. Neither compound 1 at a dose of 0.01 mg/kg nor donepezil at a dose of 0.1 mg/kg were found to have a significant effect when administered alone. However, the same doses of compound 1 and donepezil, when formulated together in 5% DMSO and 95% sterile saline, resulted in a noticeable attenuation of the scopolamine-induced cognitive decline.

Example 4

The Effect of Compound 2 on Scopolamine-Induced Cognitive Impairment

Figure 5:
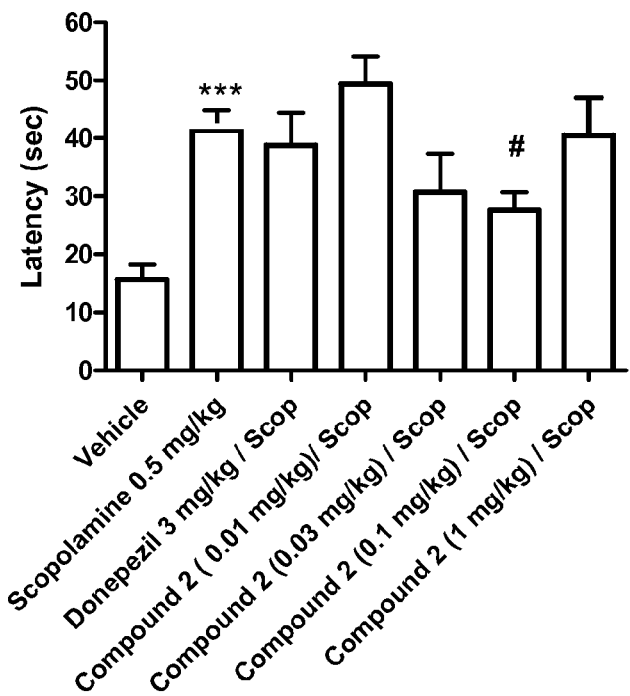

Compound 2 was tested as described in Example 1. As illustrated in FIG. 5, the effect of compound 2 at a dose of 0.1 mg/kg, achieved statistical significance with respect to scopolamine. A "U-shaped" dose-response curve was evident; the highest dose of compound 2, 1 mg/kg, had no effect on the scopolamine-induced response unlike the 0.03 and 0.1 mg/kg doses. Compound 2 (0.1 mg/kg i.p.) produced a similar reversal to that of donepezil (3 mg/kg i.p.) on day 3 (i.e., in the range of 50-60%, see FIG. 1).

Example 5

The Effect of Compound 2 Together with a 5-HT$_4$ Receptor Antagonist on Scopolamine-Induced Cognitive Impairment The effect of co-administration of compound 2 with the 5-HT$_4$ receptor antagonist GR125487 was probed as described in Example 2. Adding GR125487 (1 mg/kg i.p.) abolished the ability of compound 2 (0.1 mg/kg i.p.) to reverse scopolamine-induced cognitive impairment, which indicates the observed effects of compound 2 are due to 5-HT$_4$ receptor agonism.

Example 6

Figure 6:
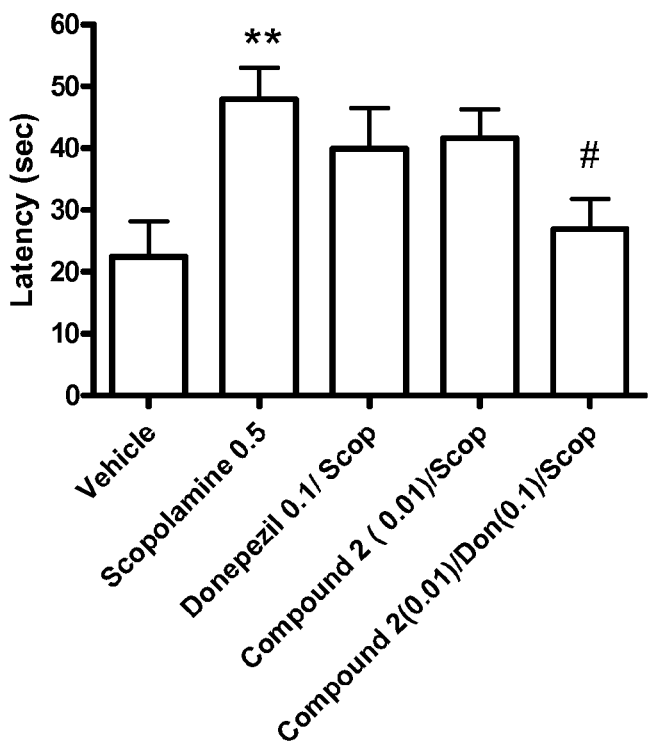

The Effect of Co-Administration of Compound 2 Together with a the Acetylcholinesterase Inhibitor Donepezil on Scopolamine-Induced Cognitive Impairment The effect of co-administration of compound 2 and donepezil is illustrated in FIG. 6. Neither compound 2 at a dose of 0.01 mg/kg nor donepezil at a dose of 0.1 mg/kg were found to have a significant effect when administered alone. However, the same doses of compound 2 and donepezil, when formulated together in 5% DMSO and 95% sterile saline, resulted in a statistically significant reversal (student t-test with Bonferroni adjustment p<0.025) of the scopolamine-induced cognitive decline.

Example 7

In Vitro Study of Effects of Compound 1 and Compound 2 on Extracellular Release of sAPPα in HEK293-5-HT$_{4(d)}$-APP$_{695}$ Cells Cell Culture HEK-293 (human embryonic kidney) cells stably-transfected with human 5-HT$_{4(d)}$ receptor cDNA and human APP$_{695}$ cDNA (HEK293-5-HT$_{4(d)}$-APP$_{695}$) were grown in Dulbecco's Modified Eagles Medium (DMEM) containing D-glucose supplemented with 10% fetal bovine serum, 2 mM GlutaMax-1, and 100 units penicillin (100 μg), and 100 μg/mL streptomycin in a 5% CO$_2$, humidified incubator at 37° C. Cells were grown under continuous selection pressure by the addition of G418 (500 ug/mL) antibiotic.

sAPPα Release

HEK293-5-HT$_{4(d)}$-APP$_{695}$ cells (3×10$^5$ cells/well) were serum-starved for 4 hr prior to incubation with agonists for 30 min (unless otherwise stated) at 37° C. The culture medium was aspirated, centrifuged to remove cellular debris and the level of sAPPα determined by Western blot. sAPPα was detected using antibody 6E10 (Signet/Covance) and a goat anti-mouse HRP-conjugated 2° antibody. Immunoreactive bands corresponding to sAPPα were visualized and quantified with ECL substrate (Pierce) and a Fluor Chem HD2 image system (Alpha Innotech). Western blot analysis of samples was conducted in duplicate.

Results

Potency data are reported as pEC$_{50}$ values, the negative decadic logarithm of the EC$_{50}$ value, where EC$_{50}$ is the effective concentration for a 50% maximal response. Test compounds exhibiting a higher pEC$_{50}$ value in this assay have a higher potency for stimulating sAPPα release. To determine EC$_{50}$ values, data from independent experiments were fit simultaneously to a sigmoidal concentration response curve using Graph Pad Prism software (slope constrained to unity). Potency data for compound 1 and compound 2, together with the percentage response relative to the effect of the endogenous ligand 5-HT at a concentration of 1 μM are given below:

|  | pEC$_{50}$ | E$_{max}$ (% response relative to 1 μM 5-HT) |
| --- | --- | --- |
| Compound 1 | 8.2 | 91 |
| Compound 2 | 9.0 | 103 |

The effect of the 5-HT$_4$ receptor-selective antagonist GR113808 was probed by incubating the cells for 10 min with 1 μM GR113808 before incubating with compound 1 or compound 2 at a concentration of 100 nM, a concentration at which the compounds evoked a near-maximal or maximal response. The antagonist completely blocked the effect of compound 1 and of compound 2, indicating that the observed release of sAPPα is related to agonism of the 5-HT$_4$ receptor.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A method of treating Alzheimer's disease or a cognitive disorder in a patient, the method comprising administering to the patient in need thereof a combination of a 5-HT$_4$ receptor agonist compound wherein the 5-HT$_4$ receptor agonist compound is 1-isopropyl-2-oxo-1,2- dihydroquinoline -3-carboxylic acid {(1S,3R,5R)-8-[(R)-2-hydroxy-3-(methanesulfonyl- methyl -amino)propyl]-8-azabicyclo[3.2.1]oct-3-yl}amide or a pharmaceutically acceptable salt thereof and donepezil hydrochloride, wherein the 5-HT$_4$ receptor agonist compound and the donepezil hydrochloride are each administered at a dose that is subefficacious for treating Alzheimer's disease or a cognitive disorder when administered alone.

2. The method of claim 1 wherein the 5-HT$_4$ receptor agonist compound is 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo [3.2.1]oct-3-yl} amide hydrochloride.

3. A method of enhancing memory in a patient experiencing a memory deficit, the method comprising administering to the patient in need thereof a combination of a 5-HT$_4$ receptor agonist compound wherein the 5-HT$_4$ receptor agonist compound is 1-isopropyl-2-oxo-1,2- dihydroquinoline -3-carboxylic acid {(1S,3R,5R)-8-[(R)-2-hydroxy-3-(methanesulfonyl- methyl -amino)propyl]-8-azabicyclo[3.2.1]oct-3-yl}amide or a pharmaceutically acceptable salt thereof and donepezil hydrochloride, wherein the 5-HT$_4$ receptor agonist compound and the donepezil hydrochloride are each administered at a dose that is subefficacious for enhancing memory in a patient experiencing a memory deficit, when administered alone.

4. The method of claim 3 wherein the 5-HT$_4$ receptor agonist compound is 1-isopropyl-2-oxo-1,2-dihydroquinoline-3-carboxylic acid {(1S,3R,5R)-8-[(R)-2-hydroxy-3-(methanesulfonyl -methyl-amino)propyl]-8-azabicyclo [3.2.1]oct-3-yl} amide hydrochloride.

* * * * *